US012708639B2

(12) United States Patent
De Marchi et al.

(10) Patent No.: US 12,708,639 B2
(45) Date of Patent: Aug. 18, 2026

(54) COMPOSITIONS AND METHODS TO TREAT OR PREVENT METABOLIC FATIGUE USING THE COMPOUND OLEUROPEIN OR A METABOLITE THEREOF

(71) Applicant: SOCIETE DES PRODUITS NESTLE S.A., Vevey (CH)

(72) Inventors: Umberto De Marchi, Corminboeuf (CH); Marie Noelle Horcajada, Echenevex (FR); Jerome Feige, Crissier (CH); Cristina Mammucari, Padua (IT); Bert Blaauw, Padua (IT)

(73) Assignee: Societe des Produits Nestle S.A., Vevey (CH)

( * ) Notice: Subject to any disclaimer, the term of this patent is extended or adjusted under 35 U.S.C. 154(b) by 1079 days.

(21) Appl. No.: 17/595,166

(22) PCT Filed: May 13, 2020

(86) PCT No.: PCT/EP2020/063329
§ 371 (c)(1),
(2) Date: Nov. 10, 2021

(87) PCT Pub. No.: WO2020/229538
PCT Pub. Date: Nov. 19, 2020

(65) Prior Publication Data

US 2022/0202842 A1 Jun. 30, 2022

Related U.S. Application Data

(60) Provisional application No. 62/847,076, filed on May 13, 2019.

(51) Int. Cl.
*A61K 31/7048* (2006.01)
*A23L 33/125* (2016.01)
*A61P 43/00* (2006.01)

(52) U.S. Cl.
CPC ........ *A61K 31/7048* (2013.01); *A23L 33/125* (2016.08); *A61P 43/00* (2018.01)

(58) Field of Classification Search
CPC ........................... A61K 31/7048; A61P 43/00
See application file for complete search history.

(56) References Cited

U.S. PATENT DOCUMENTS 2,707,152 A * 4/1955 Chaney .................. A23C 9/146 426/271
10,751,357 B2 * 8/2020 Horcajada ............ A61K 31/352
11,364,254 B2 * 6/2022 Horcajada ............... A61P 21/06
11,813,273 B2 * 11/2023 Horcajada ............. A23L 33/105
2006/0193931 A1 8/2006 Coxam et al.
2011/0112201 A1 5/2011 Liu et al.
2012/0302645 A1 * 11/2012 Liu .......................... A23L 2/52 514/731
2013/0059920 A1 3/2013 Friedel et al.
2016/0045519 A1 * 2/2016 Horcajada ............ A61K 31/593 514/27
2018/0353527 A1 12/2018 Horcajada et al.

FOREIGN PATENT DOCUMENTS

CA 3224027 A1 * 5/2017 ........... A23L 33/105
CN 106213492 A * 12/2016
EP 1072265 A1 1/2001
JP 2017178914 A 10/2017
WO WO-0245524 A2 * 6/2002 ............. A23L 33/18
WO 2009121600 A2 10/2009
WO 2010118789 10/2010
WO 2014161872 A1 10/2014
WO 2015063737 A1 5/2015
WO 2019092069 A2 5/2019
WO 2020229538 A1 11/2020
WO 2020229539 A1 11/2020

OTHER PUBLICATIONS

U.S. Appl. No. 17/736,496, filed May 13, 2019, De Marchi; Umberto, A61K31/7048, 1/1.*
Hatton et al., The human cell count and size distribution, Proc Natl Acad Sci U S A, Sep. 26, 2023; 120(39).*
Hunter, n-3 fatty acids from vegetable oils, Am J Clin Nutr, 1990.*
Food Sources of Vitamin D, Data Source: U.S. Department of Agriculture, Agricultural Research Service. FoodData Central, 2019, fdc.nal.usda.gov, available at https://www.dietaryguidelines.gov/resources/2020-2025-dietary-guidelines-online-materials/food-sources-select-nutrients/food-sources-vitamin-d.*
Fujiwara et al., Oleuropein improves insulin resistance in skeletal muscle by promoting the translocation of GLUT4, J Clin Biochem Nutr. Nov. 2017;61(3):196-202.*
Doehner et al., Skeletal muscle weakness is related to insulin resistance in patients with chronic heart failure, ESC Heart Fail, Jun. 2015;2(2):85-89.*
Van Sickle et al., Lipids, vol. 27, No. 3, pp. 157-160, 1992.*
Notification of Transmittal of the International Search Report and the Written Opinion for International Appl No. PCT/EP2023/061479 dated Aug. 4, 2023.
Chinese Office Action for Appl No. 202080029054.4 dated May 13, 2023.
Marchetti et al. "Oleuropein-Enriched Olive Leaf Extract Affects Calcium Dynamics and Impairs Viability of Malignant Mesothelioma Cells" Hindawi Publishing Corporation Evidence-Based Complementary and Alternative Medicine, 2015, Article ID 908493, 9 pages.

(Continued)

*Primary Examiner* — Svetlana M Ivanova
(74) *Attorney, Agent, or Firm* — K&L Gates LLP

(57) ABSTRACT

At least one of oleuropein or metabolite thereof can be orally administered to an individual in an amount effective to achieve at least one result that is one or more of (i) improvement in a physiological state linked to metabolic fatigue in one or more cells, (ii) increased mitochondrial energy and mitochondrial calcium uptake in one or more cells, and/or (iii) treatment or prevention of a calcium deficiency/depletion disorder. Additionally or alternatively, the method can treat or prevent a mitochondria-related disease or a condition associated with altered mitochondrial function in an individual in need thereof or at risk thereof.

10 Claims, 16 Drawing Sheets

(56) References Cited

OTHER PUBLICATIONS

Van Dronkelaar et al. "Minerals and Sarcopenia: The Role of Calcium, Iron, Magnesium, Phosphorus, Potassium, Selenium, Sodium, and Zinc on Muscle Mass, Muscle Strength, and Physical Performance in Older Adults: A Systematic Review" JAMDA, 2017, vol. 19, pp. 1-9.
Filip et al., "Twelve-Month Consumption of a Polyphenol Extract From Olive (*Olea europaea*) in a Double Blind, Randomized Trial Increases Serum Total Osteocalcin Levels and Improves Serum Lipid Profiles in Postmenopausal Women With Osteopenia", The Journal of Nutrition, Health & Aging, vol. 19, Issue No. 1, 2015, pp. 77-86.
Fernandez-Real et al., "A Mediterranean Diet Enriched With Olive Oil is Associated with Higher Serum Total Osteocalcin Levels in Elderly Men at High Cardiovascular Risk", The Journal of Clinical Endocrinology & Metabolism, vol. 97, Issue No. 10, 2012, pp. 3792-3798.
Hutchins-Wiese et al., "The Impact of Supplemental N-3 Long Chain Polyunsaturated Fatty Acids and Dietary Antioxidants on Physical Performance in Postmenopausal Women", The Journal of Nutrition, Health and Aging, vol. 17, Issue No. 1, 2013, pp. 76-80.
Application for the Approval of Bonolive® (Standardised Olive Leaf Extract), Retrieved from <https://acnfp.food.gov.uk/sites/default/files/bonolive.nonconf.pdf>, Dec. 15, 2016, 77 Pages.
"Peach and Mango Flavour Ultra Concentrated Pre-Workout Formula", Mintel, Record Id 5075085, 2017, 2 Pages.
Australian Office Action for Appl No. 2020273559 dated Jul. 21, 2025, 7 pages.
Bulotta et al., "Beneficial Effects of the Olive Oil Phenolic Components Oleuropein and Hydroxytyrosol: Focus on Protection against Cardiovascular and Metabolic Diseases", Journal of Translational Medicine, vol. 12, 2014, pp. 1-9.
Japanese Office Action for Appl No. 2021-565841 dated Aug. 12, 2025, 3 pages.

* cited by examiner

OH
$OCH_3$
3
OH

COMPOSITIONS AND METHODS TO TREAT OR PREVENT METABOLIC FATIGUE USING THE COMPOUND OLEUROPEIN OR A METABOLITE THEREOF

CROSS REFERENCE TO RELATED APPLICATIONS

The present application is a National Stage of International Application No. PCT/EP2020/063329, filed on May 13, 2020, which claims priority to U.S. Provisional Patent Application No. 62/847,076, filed on May 13, 2019, the entire contents of which are being incorporated herein by reference.

BACKGROUND

The present disclosure generally relates to compositions and methods that use at least one of oleuropein or metabolite thereof to manage energy at a cellular level. The compositions and methods can boost mitochondrial function and increase bioenergetics through activation of the mitochondrial calcium uniporter to thereby promote cellular activation.

Sarcopenia is defined as the age-associated loss of muscle mass and functionality (including muscle strength and gait speed). Muscle functionality and physical ability decline with the loss of muscle mass. Impaired muscle functionality is highly predictive of the incidence of immobility, disability, and mortality in advanced age. With the rising elderly population, sarcopenia becomes increasingly prevalent such that 45% of the elderly U.S. population has moderate-to-severe symptoms. The U.S. health care direct and indirect costs attributable to sarcopenia reach nearly $19 billion. Therefore, prevention and/or treatment of sarcopenia would have a great impact on the health and quality of life of our society and consequently on the economy associated with health care. Unfortunately, the etiology and the physiopathological mechanism of sarcopenia are still poorly understood, making effective measures for prevention or treatment difficult.

SUMMARY

Mitochondria are the primary source of aerobic energy production in mammalian cells and also maintain a large $Ca^{2+}$ gradient across their inner membrane, providing a signaling potential for this molecule. Furthermore, mitochondrial $Ca^{2+}$ plays a role in the mitochondria in the regulation of ATP generation and potentially contributes to the orchestration of cellular metabolic homeostasis. (Glancy, B. and R. S. Balaban (2012). "Role of mitochondrial Ca2+ in the regulation of cellular energetics." Biochemistry 51(14): 2959-2973).

In view of the experimental data disclosed later herein, the present inventors believe that oleuropein enhances the efficiency of mitochondria to produce energy, and optional calcium may enhance this effect from the oleuropein.

Accordingly, in a general embodiment, the present disclosure provides a method of achieving at least one result selected from the group consisting of (i) improvement in a physiological state linked to metabolic fatigue in one or more cells, (ii) increased mitochondrial energy and mitochondrial calcium uptake in one or more cells, and (iii) treatment or prevention of a calcium deficiency/depletion disorder. The method comprises orally administering to an individual an effective amount of at least one of oleuropein or metabolite thereof.

In an embodiment, at least a portion of the one or more cells are part of at least one body part selected from the group consisting of a liver, a kidney, a brain, and a skeletal muscle.

In an embodiment, the physiological state linked to metabolic fatigue comprises muscle fatigue or weakness, lack of energy, physical energy, lack of vitality or weakness.

In an embodiment, the effective amount of at least one of oleuropein or metabolite thereof is administered daily for at least one week.

In an embodiment, the metabolite of oleuropein is selected from the group consisting of oleuropein aglycone, hydroxytyrosol, homovanillyl alcohol, isohomovanillyl alcohol, glucuronidated forms thereof, sulfated forms thereof, derivatives thereof, and mixtures thereof.

In an embodiment, the effective amount of at least one of oleuropein or metabolite thereof is administered in a composition selected from the group consisting of food compositions, beverages, dietary supplements, nutritional compositions, nutraceuticals, powdered nutritional products to be reconstituted in water or milk before consumption, food additives, medicaments, drinks, petfood, and combinations thereof.

In an embodiment, the at least one of oleuropein or metabolite thereof is administered in a composition further comprising calcium.

In an embodiment, the effective amount of at least one of oleuropein or metabolite thereof is administered in a food product further comprising a component selected from the group consisting of protein, carbohydrate, fat and mixtures thereof.

In another embodiment, the present disclosure provides a method of treating or preventing (e.g., reducing incidence and/or severity) a mitochondria-related disease or a condition associated with altered mitochondrial function in an individual in need thereof or at risk thereof. The method comprises orally administering to the individual an effective amount of at least one of oleuropein or metabolite thereof.

The mitochondria-related disease or condition can be selected from the group consisting of stress, physiological ageing, obesity, reduced metabolic rate, metabolic syndrome, diabetes mellitus, complications from diabetes, hyperlipidemia, neurodegenerative disease, cognitive disorder, stress-induced or stress-related cognitive dysfunction, mood disorder, anxiety disorder, age-related neuronal death or dysfunction, chronic kidney disease, kidney failure, trauma, infection, cancer, hearing loss, macular degeneration, myopathies and dystrophies, and combinations thereof.

In an embodiment, the at least one of oleuropein or metabolite thereof is administered in a composition further comprising calcium.

In another embodiment, the present disclosure provides a unit dosage form comprising at least one of oleuropein or metabolite thereof in an amount effective for at least one result selected from the group consisting of (i) improvement in a physiological state linked to metabolic fatigue in one or more cells, (ii) increased mitochondrial energy and mitochondrial calcium uptake in one or more cells, and (iii) treatment or prevention of a calcium deficiency/depletion disorder (e.g., reduction in incidence and/or severity). At least a portion of the one or more cells can be part of at least one body part selected from the group consisting of a liver, a kidney, a brain, and a musculoskeletal muscle.

In an embodiment, the physiological state linked to metabolic fatigue comprises muscle fatigue or weakness, lack of energy, physical energy, lack of vitality or weakness.

In an embodiment, the unit dosage form consists essentially of the at least one of oleuropein or metabolite thereof.

In an embodiment, the unit dosage form consists of an excipient and the at least one of oleuropein or metabolite thereof.

In an embodiment, the unit dosage form further comprises calcium. The unit dosage form can consist essentially of the calcium and the at least one of oleuropein or metabolite thereof. The unit dosage form can consist of an excipient, the calcium, and the at least one of oleuropein or metabolite thereof.

In another embodiment, the present disclosure provides a method of making a composition for achieving at least one result selected from the group consisting of (i) improvement in a physiological state linked to metabolic fatigue in one or more cells, (ii) increased mitochondrial energy and mitochondrial calcium uptake in one or more cells, and (iii) treatment or prevention of a calcium deficiency/depletion disorder (e.g., reduction in incidence and/or severity). The method comprises adding an effective amount of at least one of oleuropein or metabolite thereof to at least one ingredient selected from the group consisting of protein, carbohydrate, and fat. At least a portion of the one or more cells can be part of at least one body part selected from the group consisting of a liver, a kidney, a brain, and a skeletal muscle.

In an embodiment, the method further comprises adding calcium to the at least one ingredient.

In an embodiment, the method further comprises adding to the at least one ingredient a food additive selected from the group consisting of acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers, vitamins, minerals and combinations thereof.

Additional features and advantages are described herein and will be apparent from the following Figures and Detailed Description.

DETAILED DESCRIPTION

Definitions

Figure 1:
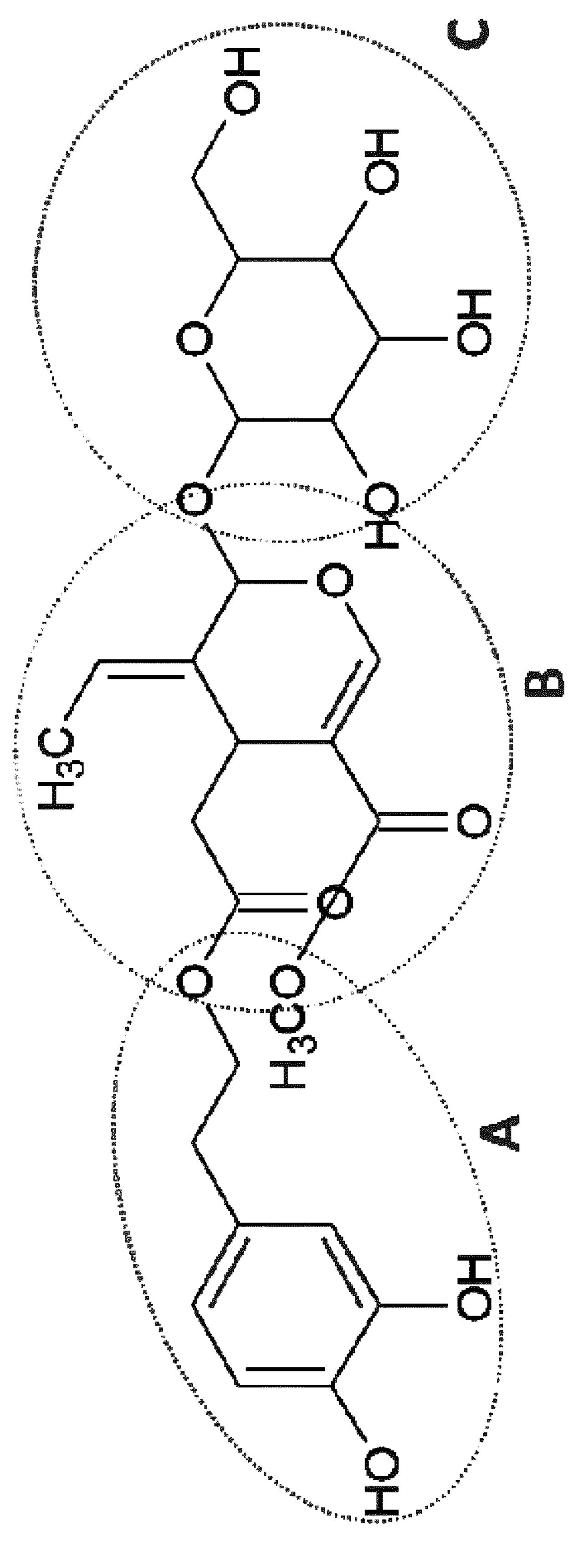
FIG. 1 shows the chemical structure of oleuropein.

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a metabolite" or "the metabolite" includes one metabolite but also two or more metabolites.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified.

As used herein, a "composition consisting essentially of at least one of oleuropein or metabolite thereof" and a "composition consisting essentially of calcium and at least one of oleuropein or metabolite thereof" do not include any additional compound that affects mitochondrial calcium import other than the at least one of oleuropein or metabolite thereof and the optional calcium. In a particular non-limiting embodiment, the composition consists of an excipient, the at least one of oleuropein or metabolite thereof, and optionally calcium.

The term "and/or" used in the context of "X and/or Y" should be interpreted as "X," or "Y," or "X and Y." Similarly, "at least one of X or Y" should be interpreted as "X," or "Y," or "both X and Y." For example, "at least one of oleuropein or metabolite thereof" means "oleuropein," or "a metabolite of oleuropein," or "both oleuropein and a metabolite thereof."

Where used herein, the terms "example" and "such as," particularly when followed by a listing of terms, are merely exemplary and illustrative and should not be deemed to be exclusive or comprehensive. As used herein, "associated with" and "linked with" mean occurring concurrently, preferably means caused by the same underlying condition, and most preferably means that one of the identified conditions is caused by the other identified condition.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the elements disclosed herein, as well as any additional or optional ingredients, components, or elements described herein or otherwise useful in a diet.

As used herein, the terms "treat" and "treatment" mean to administer a composition as disclosed herein to a subject having a condition in order to lessen, reduce or improve at least one symptom associated with the condition and/or to slow down, reduce or block the progression of the condition. The terms "treatment" and "treat" include both prophylactic or preventive treatment (that prevent and/or slow the development or progression of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

Both human and veterinary treatments are within the scope of the present disclosure. Preferably the at least one of oleuropein or metabolite thereof is administered in a serving or unit dosage form that provides a therapeutically effective or prophylactically effective amount.

The terms "prevent" and "prevention" mean to administer a composition as disclosed herein to a subject is not showing any symptoms of the condition to reduce or prevent development of at least one symptom associated with the condition. Furthermore, "prevention" includes reduction of risk, incidence and/or severity of a condition or disorder.

As used herein, an "effective amount" is an amount that treats or prevents a deficiency, treats or prevents a disease or medical condition in an individual, or, more generally, reduces symptoms, manages progression of the disease, or provides a nutritional, physiological, or medical benefit to the individual.

The relative terms "improved," "increased," "enhanced" and the like refer to the effects of the composition disclosed herein, namely a composition comprising an effective amount of at least one of oleuropein or metabolite thereof, relative to administration over the same time period of a composition lacking oleuropein and lacking an oleuropein metabolite but otherwise identical.

As used herein, "administering" includes another individual providing a referenced composition to an individual so that the individual can consume the composition and also includes merely the act of the individual themselves consuming a referenced composition.

"Animal" includes, but is not limited to, mammals, which includes but is not limited to rodents; aquatic mammals; domestic animals such as dogs, cats and other pets; farm animals such as sheep, pigs, cows and horses; and humans. Where "animal," "mammal" or a plural thereof is used, these terms also apply to any animal that is capable of the effect exhibited or intended to be exhibited by the context of the passage, e.g., an animal benefitting from improved mitochondrial calcium import. While the term "individual" or "subject" is often used herein to refer to a human, the present disclosure is not so limited. Accordingly, the term "individual" or "subject" refers to any animal, mammal or human that can benefit from the methods and compositions disclosed herein.

The term "pet" means any animal which could benefit from or enjoy the compositions provided by the present disclosure. For example, the pet can be an avian, bovine, canine, equine, feline, hircine, lupine, murine, ovine, or porcine animal, but the pet can be any suitable animal. The term "companion animal" means a dog or a cat.

The term "elderly" in the context of a human means an age from birth of at least 60 years, preferably above 63 years, more preferably above 65 years, and most preferably above 70 years. In the context of non-human animals, "elderly" means a non-human subject that has reached 60% of its likely lifespan, in some embodiments at least 70%, at least 80% or at least 90% of its likely lifespan. A determination of lifespan may be based on actuarial tables, calculations, or estimates, and may consider past, present, and future influences or factors that are known to positively or negatively affect lifespan. Consideration of species, gender, size, genetic factors, environmental factors and stressors, present and past health status, past and present nutritional status, and stressors may be taken into consideration when determining lifespan. The term "older adult" in the context of a human means an age from birth of at least 45 years, preferably above 50 years, more preferably above 55 years, and includes elderly individuals.

The terms "serving" or "unit dosage form," as used herein, are interchangeable and refer to physically discrete units suitable as unitary dosages for human and animal subjects, each unit containing a predetermined quantity of the composition comprising at least one of oleuropein or metabolite thereof, as disclosed herein, in an amount sufficient to produce the desired effect, preferably in association with a pharmaceutically acceptable diluent, carrier or vehicle. The specifications for the unit dosage form depend on the particular compounds employed, the effect to be achieved, and the pharmacodynamics associated with each compound in the host. In an embodiment, the unit dosage form can be a predetermined amount of liquid housed within a container such as a bottle.

An "oral nutrition supplement" or "ONS" is a composition comprising at least one macronutrient and/or at least one micronutrient, for example in a form of sterile liquids, semi-solids or powders, and intended to supplement other nutritional intake such as that from food. Non-limiting examples of commercially available ONS products include MERI IENE®, BOOST®, NUTREN® and SUSTAGEN®. In some embodiments, an ONS can be a beverage in liquid form that can be consumed without further addition of liquid, for example an amount of the liquid that is one serving of the composition.

As used herein, "incomplete nutrition" refers to preferably nutritional products that do not contain sufficient levels of macronutrients (protein, fats and carbohydrates) or micronutrients to be sufficient to be a sole source of nutrition for the animal to which the nutritional product is being administered. The term "complete nutrition" refers to a product which is capable of being the sole source of nutrition for the subject. An individual can receive 100% of their nutritional requirements from a complete nutrition composition.

A "kit" means that the components of the kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof.

"Metabolic fatigue" means reduced mitochondrial function in one or more cells (e.g., one or more of liver, kidney, brain, skeletal muscle) due to a shortage of substrates within the one or more cells and/or an accumulation of metabolites within the muscle fiber which interfere either with the release of calcium or with the ability of calcium to stimulate mitochondrial function. Physiological states linked to metabolic fatigue may comprise muscle fatigue or weakness, lack of energy, in particular physical energy, lack of vitality or weakness.

EMBODIMENTS

Figure 2:
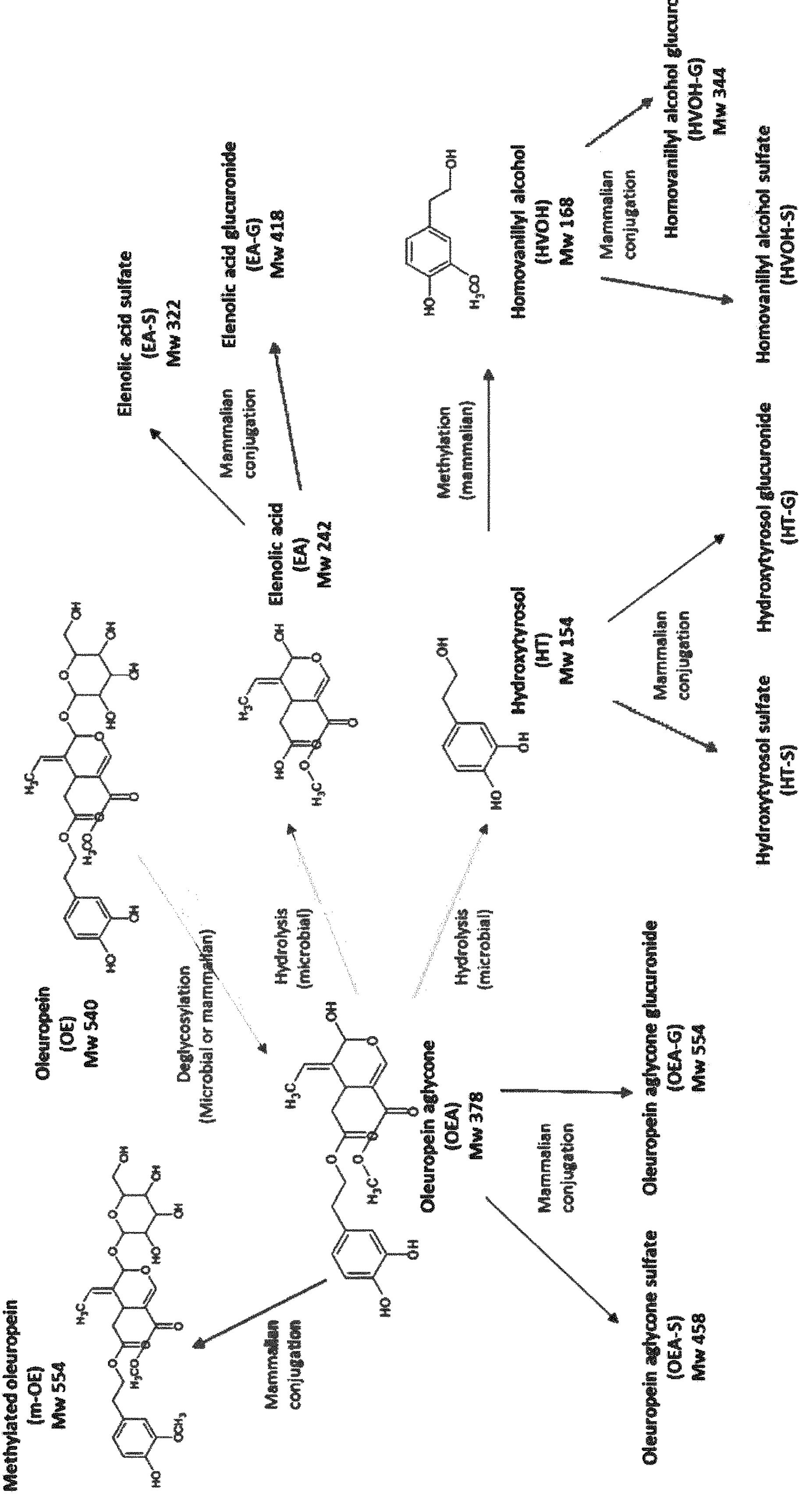
FIG. 2 shows the proposed metabolism pathway of oleuropein by mammalian and microbial enzymes, based on the findings reported in the literature.

Oleuropein is a polyphenol found in the fruit, the roots, the trunk and more particularly in the leaves of plants belonging to the Oleaceae family, and especially *Olea europaea*. FIG. 1 shows the chemical structure of oleuropein. Oleuropein is a heterosidic ester of 3,4-dihydroxyphenylethanol (also known as hydroxytyrosol, labeled as "A" in FIG. 1) and elenolic acid (labeled as "B" in FIG. 1) containing a molecule of glucose (labeled as "C" in FIG. 1). FIG. 2 shows a proposed metabolism pathway of oleuropein by mammalian and microbial enzymes, based on the findings reported in the literature.

An aspect of the present disclosure is a method of achieving at least one result selected from the group consisting of (i) improvement in a physiological state linked to metabolic fatigue in one or more cells, (ii) increased mitochondrial energy and mitochondrial calcium uptake in one or more cells, and (iii) treatment or prevention of a calcium deficiency/depletion disorder (e.g., reduction in incidence and/or severity). The method comprises orally administering an effective amount of at least one of oleuropein or metabolite thereof to an individual.

Another aspect of the present disclosure is a method of treating in an individual in need thereof or preventing in an individual at risk thereof (e.g., reducing incidence and/or severity) at least one condition selected from the group consisting of (i) a physiological state linked to metabolic fatigue in one or more cells and (ii) a calcium deficiency/depletion disorder. The method comprises orally administering an effective amount of at least one of oleuropein or metabolite thereof to the individual in need thereof or at risk thereof.

Yet another aspect of the present disclosure is a method of treating or preventing (e.g., reducing incidence and/or severity) a mitochondria-related disease or a condition associated with altered mitochondrial function in an individual in need thereof or at risk thereof. The method comprises orally administering to an individual an effective amount of at least one of oleuropein or metabolite thereof. The mitochondria-related disease or condition can be selected from the group consisting of stress, physiological ageing, obesity, reduced metabolic rate, metabolic syndrome, diabetes mellitus, complications from diabetes, hyperlipidemia, neurodegenerative disease, cognitive disorder, stress-induced or stress-related cognitive dysfunction, mood disorder, anxiety disorder, age-related neuronal death or dysfunction, chronic kidney disease, kidney failure, trauma, infection, cancer, hearing loss, macular degeneration, myopathies and dystrophies, and combinations thereof.

In another embodiment, metabolic fatigue comprises lack of energy, in particular physical energy, lack of vitality or weakness.

In some embodiments, the methods comprise identifying the individual as having the condition or being at risk of the condition before the administration.

The effective amount of the at least one of oleuropein or metabolite thereof varies with the particular composition, the age and condition of the recipient, and the particular disorder or disease being treated. Nevertheless, in a general embodiment, 0.001 mg to 1.0 g of the at least one of oleuropein or metabolite thereof can be administered to the individual per day, preferably from 0.01 mg to 0.9 g of the at least one of oleuropein or metabolite thereof per day, more preferably from 0.1 mg to 750 mg of the at least one of oleuropein or metabolite thereof per day, more preferably from 0.5 mg to 500 mg of the at least one of oleuropein or metabolite thereof per day, and most preferably from 1.0 mg to 200 mg of the at least one of oleuropein or metabolite thereof per day.

In some embodiments, the oleuropein is administered in a composition further comprising calcium. At least a portion of the calcium can be one or more calcium salts, such as calcium acetate, calcium carbonate, calcium chloride, calcium citrate, calcium glubionate, calcium gluconate, calcium lactate or mixtures thereof. In a general embodiment, 0.1 g to 1.0 g of the calcium is administered to the individual per day, preferably from 125 mg to 950 g of the calcium per day, more preferably from 150 mg to 900 mg of the calcium per day, more preferably from 175 mg to 850 mg of the calcium per day, and most preferably from 200 mg-800 mg of the calcium per day.

In an embodiment, at least a portion of the oleuropein is obtained by extraction, e.g., by extraction from a plant such as a plant belonging to the Oleaceae family, preferably one or more of the stems, the leaves, the fruits or the stones of a plant belonging to the Oleaceae family such as *Olea europaea* (olive tree), a plant of genus *Ligustrum*, a plant of genus *Syringa*, a plant of genus *Fraximus*, a plant of genus *Jasminum* and a plant of genus *Osmanthus*. Additionally or alternatively, at least a portion of the oleuropein and/or metabolites can be obtained by chemical synthesis.

Figures 3A, 3B:
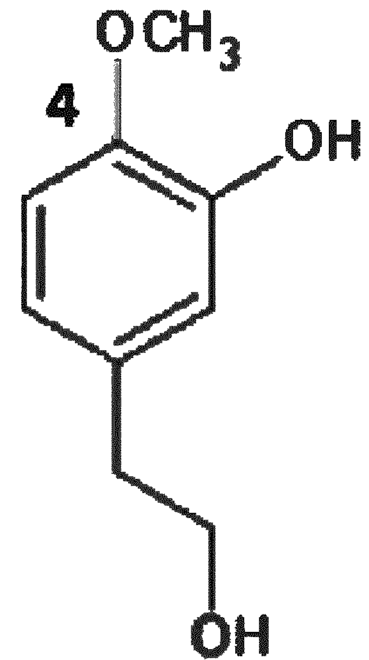
FIG. 3A shows the chemical structure of homovanillyl alcohol.
FIG. 3B shows its isomer (3-hydroxy-4-methoxyphenethanol or 3-hydroxy-4-methoxyphenethyl alcohol).

Non-limiting examples of suitable metabolites of oleuropein include oleuropein aglycone, hydroxytyrosol, homovanillyl alcohol, isohomovanillyl alcohol, glucuronidated forms thereof, sulfated forms thereof, derivatives thereof, and mixtures thereof. FIG. 3A shows the chemical structure of homovanillyl alcohol; and FIG. 3B shows its isomer (3-hydroxy-4-methoxyphenethanol or 3-hydroxy-4-methoxyphenethyl alcohol).

In some embodiments, the at least one of oleuropein or metabolite thereof is the only polyphenol in the composition and/or the only polyphenol administered to the individual.

In some embodiments, the at least one of oleuropein or metabolite thereof and the optional calcium can be administered to an elderly subject. In some embodiments, the individual is healthy. In some embodiments, the individual has metabolic fatigue, but optionally is otherwise healthy. In some embodiments, the individual can be a pet.

In an embodiment, at least a portion of the one or more cells are part of at least one body part selected from the group consisting of liver, kidney, brain and skeletal muscle.

The at least one of oleuropein or metabolite thereof and the optional calcium can be administered in any composition that is suitable for human and/or animal consumption. In a preferred embodiment, the at least one of oleuropein or metabolite thereof and the optional calcium is administered to the individual orally or enterally (e.g. tube feeding). For example, the at least one of oleuropein or metabolite thereof and the optional calcium can be administered to the individual in a beverage, a food product, a capsule, a tablet, a powder or a suspension.

Non-limiting examples of suitable compositions for the include food compositions, dietary supplements, dietary supplements (e.g., liquid ONS), complete nutritional compositions, beverages, pharmaceuticals, nutraceuticals, powdered nutritional products to be reconstituted in water or milk before consumption, food additives, medicaments, drinks, petfood, and combinations thereof.

Food products according to the present invention may include dairy products, such as fermented milk products, e.g., yoghurts, buttermilk, etc; ice creams; concentrated milk; milk; dairy creams; flavoured milk drinks; whey based drinks; toppings; coffee creamers; chocolate; cheese based products; soups; sauces; purees; dressings; puddings; custards; baby foods; nutritional formulas, such as those for complete nutrition, for example for infants, children, teenagers, adults, the elderly or the critically ill; cereals and cereal bars, for example.

Drinks may include for example milk- or yoghurt based drinks, fermented milk, protein drinks, coffee, tea, energy drinks, soy drinks, fruit and/or vegetable drinks, fruit and/or vegetable juices.

The at least one of oleuropein or metabolite thereof and the optional calcium can be administered in a food product further comprising a component selected from the group consisting of protein, carbohydrate, fat and mixtures thereof.

In some instances where oral or enteral administration is not possible or not advised, the composition may be administered parenterally.

In another embodiment, the present disclosure provides a method of treating or preventing (e.g., reducing incidence and/or severity) a mitochondria-related disease or a condition associated with altered mitochondrial function in an individual in need thereof or at risk thereof. The method comprises orally administering an effective amount of at least one of oleuropein or metabolite thereof to the individual in need thereof or at risk thereof.

In an embodiment, the at least one of oleuropein or metabolite thereof and the optional calcium is administered to the individual for a time period of at least one month; preferably at least two months, more preferably at least three, four, five or six months; most preferably for at least one year. During the time period, the at least one of oleuropein or metabolite thereof and the optional calcium can be administered to the individual at least one day per week; preferably at least two days per week, more preferably at least three, four, five or six days per week; most preferably seven days per week. The at least one of oleuropein or metabolite thereof and the optional calcium can be administered in a single dose per day or in multiple separate doses per day.

The above examples of administration do not require continuous daily administration with no interruptions. Instead, there may be some short breaks in the administration, such as a break of two to four days during the period of administration. The ideal duration of the administration of the composition can be determined by those of skill in the art.

In an embodiment, the at least one of oleuropein or metabolite thereof can be administered with calcium in the same composition, for example a unit dosage form containing both the calcium and the at least one of oleuropein or metabolite thereof.

In an alternative embodiment, the at least one of oleuropein or metabolite thereof can be administered sequentially with calcium in separate compositions. The term "sequentially" means that the calcium and the at least one of oleuropein or metabolite thereof are administered in a successive manner such that the at least one of oleuropein or metabolite thereof is administered at a first time without the calcium, and the calcium is administered at a second time (before or subsequent to the first time) without the at least one of oleuropein or metabolite thereof. The time between sequential administrations may be, for example, one or several seconds, minutes or hours in the same day; one or several days or weeks in the same month; or one or several months in the same year.

Another aspect of the present disclosure is a method of making a composition for achieving an effect selected from the group consisting of (i) improvement in a physiological state linked to metabolic fatigue in one or more cells, (ii) increased mitochondrial energy and mitochondrial calcium uptake in one or more cells, and (iii) treatment or prevention of a calcium deficiency/depletion disorder (e.g., reduction in incidence and/or severity).

The method comprises adding at least one of oleuropein or metabolite thereof to an ingredient selected from the group consisting of a protein, a carbohydrate, a lipid, and combinations thereof. The composition (e.g., food product) can be made prior to administration (e.g., the composition is made, packaged, and then purchased by a consumer who administers the composition to themselves or to another individual) or can be made substantially simultaneous to administration (the composition is made less than 30 minutes before administration, preferably less than 15 minutes before administration, more preferably less than 10 minutes before administration, most preferably less than 5 minutes before administration, by an individual who administers the composition to themselves or to another individual).

The composition can comprise an effective amount of at least one of oleuropein or metabolite thereof. For example, a single serving or dose of the composition can comprise the effective amount, and a package can contain one or more of the servings or doses. Optionally the composition can further comprise calcium.

The composition can comprise a food additive selected from the group consisting of acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers, vitamins, minerals and combinations thereof.

In addition to the at least one of oleuropein or metabolite thereof and the optional calcium, the composition can further comprise a protein source from animal or plant origin, for example milk proteins, soy proteins, and/or pea proteins. In a preferred embodiment, the protein source is selected from the group consisting of whey protein; casein protein; pea protein; soy protein; wheat protein; corn protein; rice protein; proteins from legumes, cereals and grains; and combinations thereof. Additionally or alternatively, the protein source may comprise a protein from nuts and/or seeds.

The protein source preferably comprises whey protein. The whey protein may be unhydrolyzed or hydrolyzed whey protein. The whey protein may be any whey protein, for example the whey protein can be selected from the group consisting of whey protein concentrates, whey protein isolates, whey protein micelles, whey protein hydrolysates, acid whey, sweet whey, modified sweet whey (sweet whey from which the caseino-glycomacropeptide has been removed), a fraction of whey protein, and any combination thereof. In a preferred embodiment, the whey protein comprises whey protein isolate and/or modified sweet whey.

As noted above, the protein source can be from animal or plant origin, for example milk proteins, soy proteins, and/or pea proteins. In an embodiment, the protein source comprises casein. Casein may be obtained from any mammal but is preferably obtained from cow milk and preferably as micellar casein.

The composition can comprise one or more branched chain amino acids. For example, the composition can comprise leucine, isoleucine and/or valine. The protein source in the composition may comprise leucine in free form and/or leucine bound as peptides and/or proteins such as dairy, animal or vegetable proteins. In an embodiment, the composition comprises the leucine in an amount up to 10 wt % of the dry matter of the composition. Leucine can be present as D- or L-leucine and preferably the L-form. If the composition comprises leucine, the composition can be administered in a daily dose that provides 0.01 to 0.04 g of the leucine per kg body weight, preferably 0.02 to 0.035 g of the leucine per kg body weight. Such doses are particularly applicable to complete nutrition compositions, but one of ordinary skill will readily recognize how to adapt these doses for an oral nutritional supplement (ONS).

One or more other minerals additional to any calcium can be used in the composition. Non-limiting examples of suitable minerals include boron, chromium, copper, iodine, iron, magnesium, manganese, molybdenum, nickel, phosphorus, potassium, selenium, silicon, tin, vanadium, zinc, and combinations thereof.

One or more other vitamins additional to any can be used in the composition. Non-limiting examples of suitable vitamins include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), Vitamin C, Vitamin D, Vitamin E, Vitamin K, folic acid and biotin), and combinations thereof. "Vitamin" includes such compounds obtained naturally from plant and animal foods or synthetically made, pro-vitamins, derivatives thereof, and analogs thereof.

The composition may also contain a carbohydrate and/or a source of fat. Non-limiting examples of suitable fats include canola oil, corn oil and high-oleic acid sunflower oil. Non-limiting examples of suitable carbohydrates include sucrose, lactose, glucose, fructose, corn syrup solids, maltodextrins, and mixtures thereof. Additionally or alternatively, a dietary fiber may be added. Dietary fiber passes through the small intestine undigested by enzymes and functions as a natural bulking agent and laxative. Dietary fiber may be soluble or insoluble and generally a blend of the two types is preferred. Non-limiting examples of suitable dietary fibers include soy, pea, oat, pectin, guar gum, partially hydrolyzed guar gum, gum Arabic, fructo-oligosaccharides, acidic oligosaccharides, galacto-oligosaccharides, sialyl-lactose and oligosaccharides derived from animal milks. A preferred fiber blend is a mixture of inulin with shorter chain fructo-oligosaccharides. In an embodiment, the fiber content is between 2 and 40 g/L of the composition, for example between 4 and 10 g/L.

One or more food grade emulsifiers may be incorporated into the composition, such as diacetyl tartaric acid esters of mono- and di-glycerides, lecithin, and/or mono- and di-glycerides. Suitable salts and stabilizers may be included.

EXAMPLES

The following non-limiting examples present experimental data supporting the compositions and methods disclosed herein.

Example 1

To test the effect of Oleuropein, its metabolites and calcium supplementation/deficiency in living cells, the inventors measured mitochondrial calcium elevation in HeLa cells and in myotubes differentiated from both mouse C2C12 cells and human primary adult muscle cells. HeLa cells and C2C12 cells were purchased from ATCC. Human Skeletal Muscle Myoblasts (HSMM) were purchased from Lonza. HSMM were isolated from the upper arm or leg muscle tissue of normal donors and used after the second passage. HeLa cells were seeded in 96-well plates at a density of 50000 cells per well in minimal essential medium (DMEM, Gibco), high glucose, +10% fetal calf serum. C2C12 cells were seeded in 96-well plates at a density of 8000 cells per well in DMEM high glucose (Gibco)+10% fetal calf serum. Myotubes were differentiated from C2C12 cells by growing the cells in DMEM containing 2% horse serum, for 4 days. HSMM were seeded in 96-well plates at a density of 8000 cells per well in DMEM/F-12 (Gibco). Myotubes were differentiated from HSMM by growing the cells in SKM-M medium (ZenBio) containing 2% horse serum, for 4 days.

Mitochondrial calcium measurements were carried out using Hela cells or myotubes infected with the adenovirus (from Sirion biotech) expressing the mitochondrially targeted calcium sensor mitochondrial mutated aequorin (Montero et al., 2004). For aequorin reconstitution, 24 hours after infection, cells or myotubes were incubated for 2 h at room temperature (22±° C.) in standard medium (145 mM NaCl, 5 mM KCl, 1 mM $MgCl_2$, 1 mM $CaCl_2$, 10 mM glucose and 10 mM Hepes, pH 7.4) with 1 μM wild-type coelenterazine.

For treatment, compounds were directly added to the cell culture or myotubes cultures 2 hours before measurements. Luminescence was measured at the Cytation 3 cell imaging reader (Biotek) or at the FLIPR Tetra Aequorin (Molecular Devices). Calibration of the luminecsnce data into Calcium concentration was carried out using an algoritm as described previously (Alvarez & Montero, 2002). Custom module analysis based on Excel (Microsoft) and GhaphPad Prism 7.02 (GraphPad) software was used for quantification.

Figure 4:
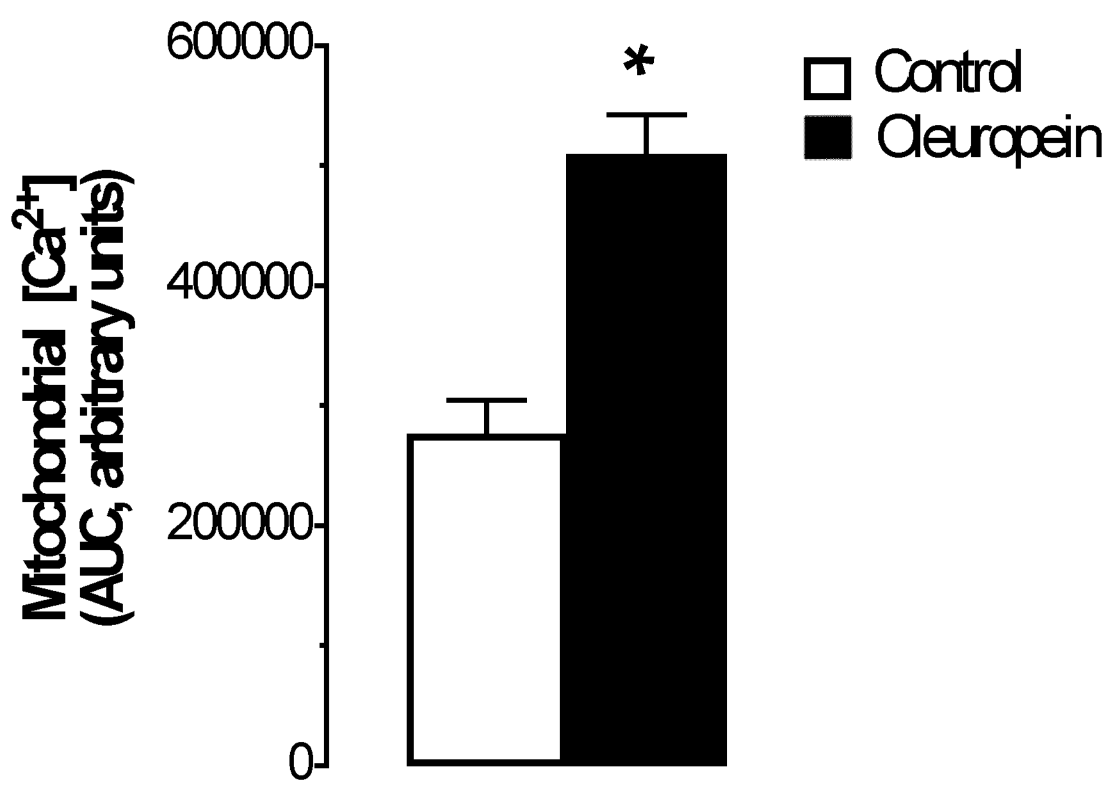
FIG. 4 is a graph showing that oleuropein increases mitochondrial calcium elevation in Hela cells, during stimulation. Statistical evaluation of the oleuropein (10 μM, black) effect on the integrated mitochondrial calcium rise, evoked by 100 μM histamine. Graph shows the average of 3 independent experiments. Results are expressed as mean+/−SEM. * indicates statistical significant difference vs. control cells (white) at $P<0.05$ (Student's t-test).
Figure 5:
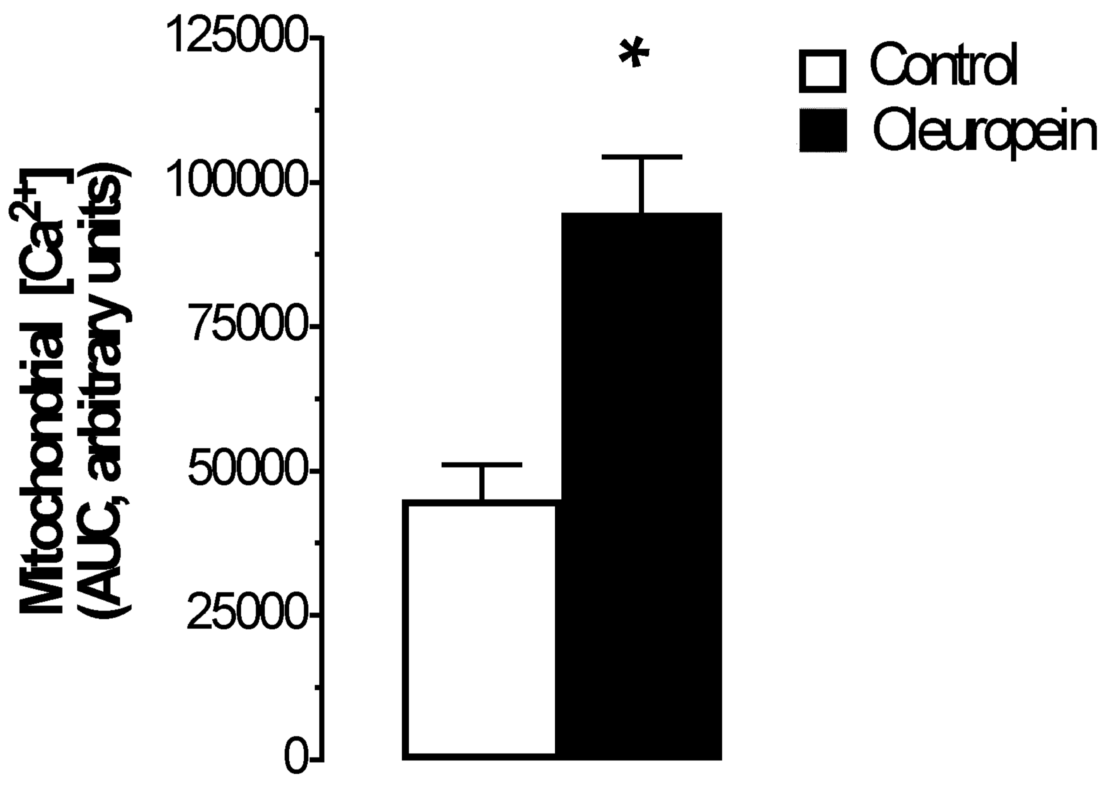
FIG. 5 is a graph showing that oleuropein enhances mitochondrial calcium in caffeine-stimulated myotubes, differentiated from human skeletal muscle myoblasts (HSMM). Statistical evaluation of the oleuropein effect (10 μM, black) on the integrated mitochondrial calcium rise, evoked by 5 mM caffeine. Graph shows the average of 6 independent experiments. Results are expressed as mean+/−SEM. * indicates statistical significant difference vs. control cells (white) at $P<0.05$ (Student's t-test).
Figure 6:
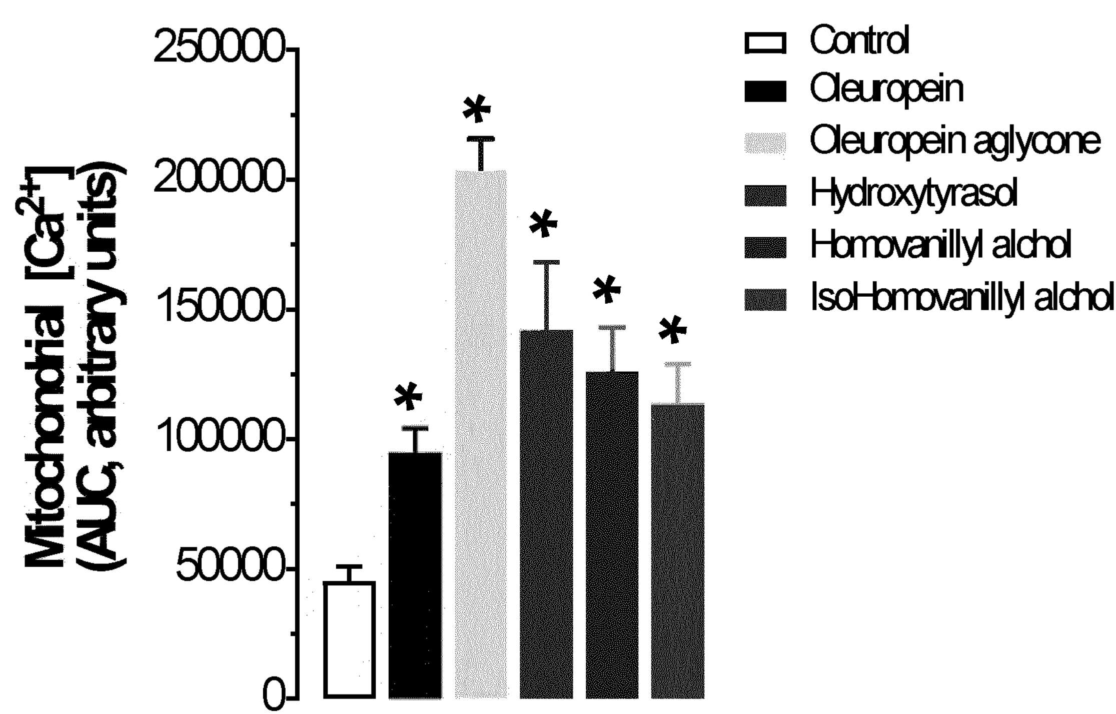
FIG. 6 is a graph showing that metabolites of oleuropein boost mitochondrial calcium in caffeine-stimulated HSMM myotubes. Statistical evaluation of the effect of oleuropein and its metabolites, at 10 μM concentration, on the integrated mitochondrial calcium rise, evoked by 5 mM caffeine. Graph shows the average of 6 independent experiments. Right, selected metabolites. Results are expressed as mean+/−SEM. * indicates statistical significant difference vs. control cells (white) at $P<0.05$ (one-way ANOVA test).
Figure 7:
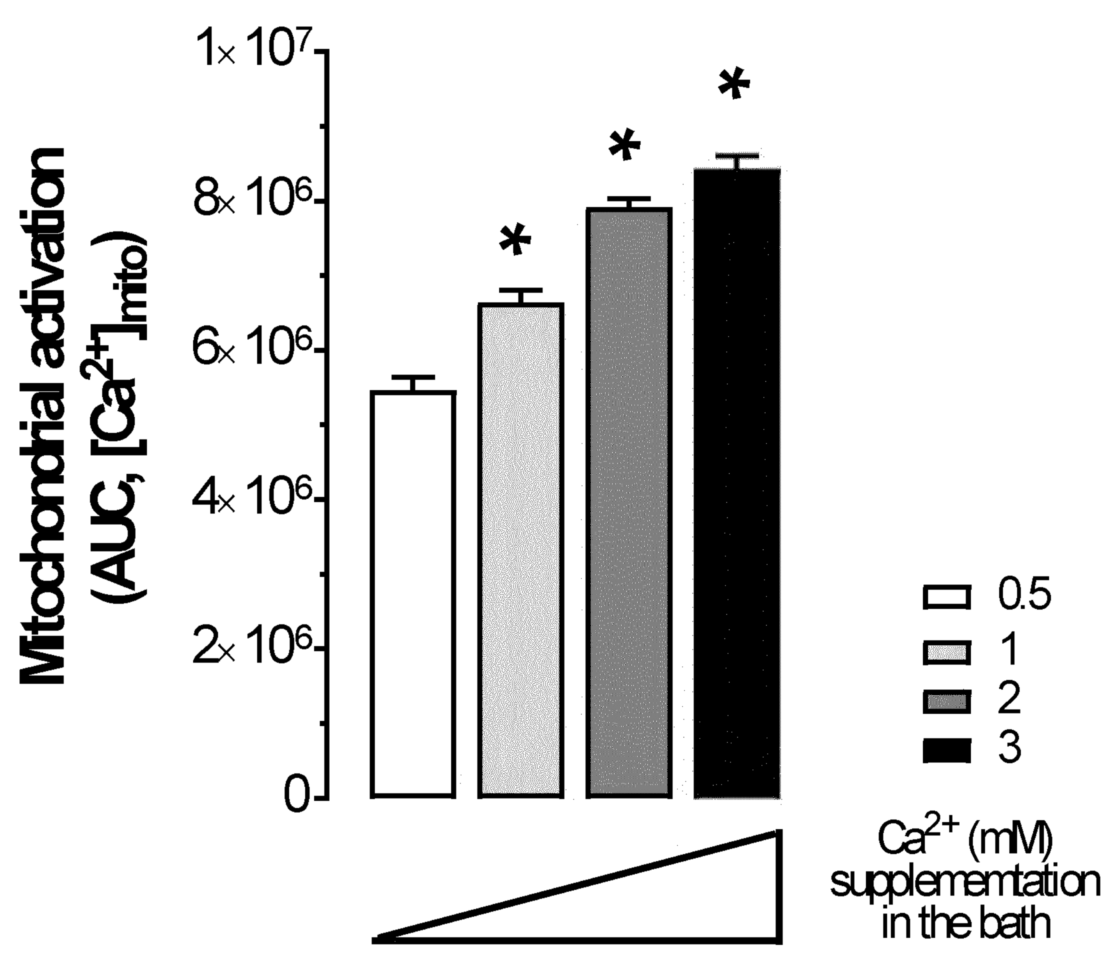
FIG. 7 is a graph showing that $Ca^{2+}$ supplementation enhances mitochondrial $Ca^{2+}$ elevation in a dose/response manner in C2C12-derived myotubes. Statistical evaluation of the effect of extracellular calcium abundance on the integrated mitochondrial calcium rise, evoked by 5 mM caffeine. Right, calcium concentration in the medium (in mM). Graph shows the average of 12 measurements from 3 independent experiments. Results are expressed as mean+/−SEM. * indicates statistical significant difference vs. 0.5 mM calcium concentration in the medium (white) at $P<0.05$ (one-way ANOVA test).
Figure 8:
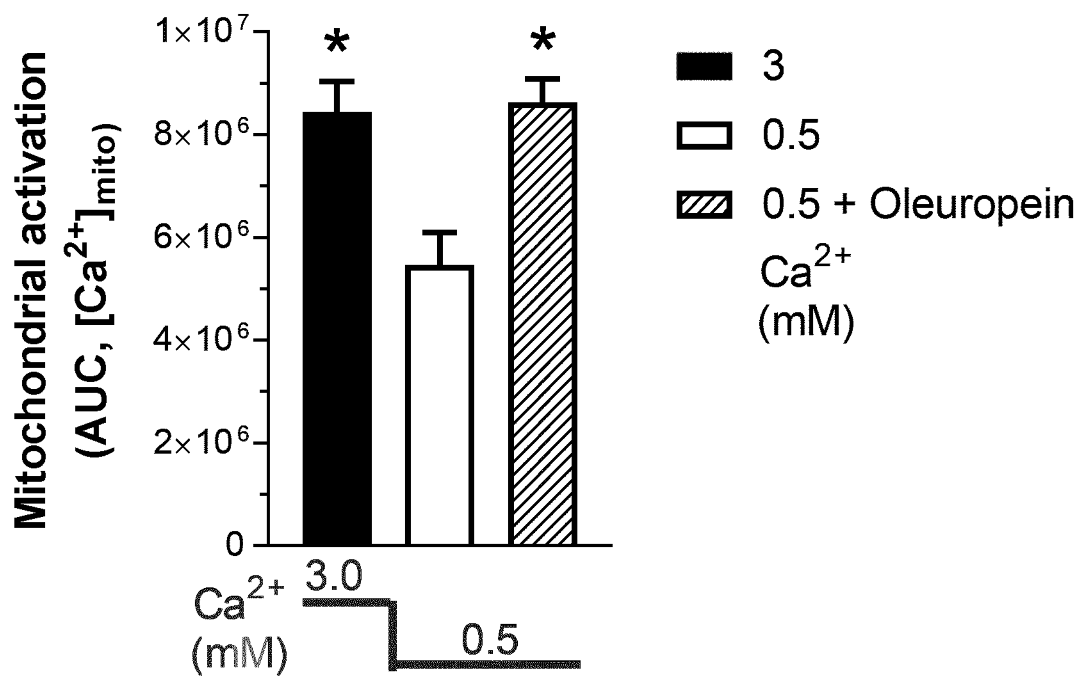
FIG. 8 is a graph showing that oleuropein rescues mitochondrial activation in calcium deficiency condition, in C2C12-derived myotubes. Statistical evaluation of the effect of 50 μM oleuropein on the integrated mitochondrial calcium rise, evoked by 5 mM caffeine. Right, calcium concentration in the medium (in mM). Graph shows the average of 12 measurements from 3 independent experiments. Results are expressed as mean+/−SEM. * indicates statistical significant difference vs. 0.5 mM calcium concentration in the medium (white) at $P<0.05$ (one-way ANOVA test).

As shown in FIG. 4, oleuropein increases mitochondrial calcium elevation in Hela cells, during stimulation. As shown in FIG. 5, oleuropein activates mitochondrial calcium in caffeine-stimulated human myotubes, differentiated from human skeletal muscle myoblasts (HSMM). As shown in FIG. 6, phenolic metabolites of oleuropein activate mitochondrial calcium in caffeine-stimulated HSMM myotubes. As shown in FIG. 7, $Ca^{2+}$ supplementation activates mitochondrial $Ca^{2+}$ elevation in a dose/response manner in C2C12-derived myotubes. As shown in FIG. 8, oleuropein rescues mitochondrial activation in calcium depletion condition, in C2C12-derived myotubes.

Example 2

To test the effect of oleuropein and hydroxytyrosol on mitochondrial respiration and to evaluate the effect of these compounds on the ATP-synthase-dependent component of the respiration, the inventors measured oxygen consumption in human skeletal muscle myotubes. For respiration experiments, oxygen consumption was measured in myotubes using a XF96 instrument (Seahorse Biosciences, MA). Human myotubes were seeded into polyornithine-coated Seahorse tissue plates at and after 2 days, the cells were washed twice in Krebs-Ringer bicarbonate Hepes buffer (KRBH), containing (in mM): 140 NaCl, 3.6 KCl, 0.5

$NaH_2PO_4$, 0.5 $MgSO_4$, 1.5 $CaCl_2$, 10 Hepes, 5 $NaHCO_3$, 10 glucose, pH 7.4. Respiration rates were determined every 6 min at 37° C. ATP synthase-dependent respiration was calculated as the difference in respiration rate before and after the addition of oligomycin. The experiments were performed at 37° C.

Figure 9:
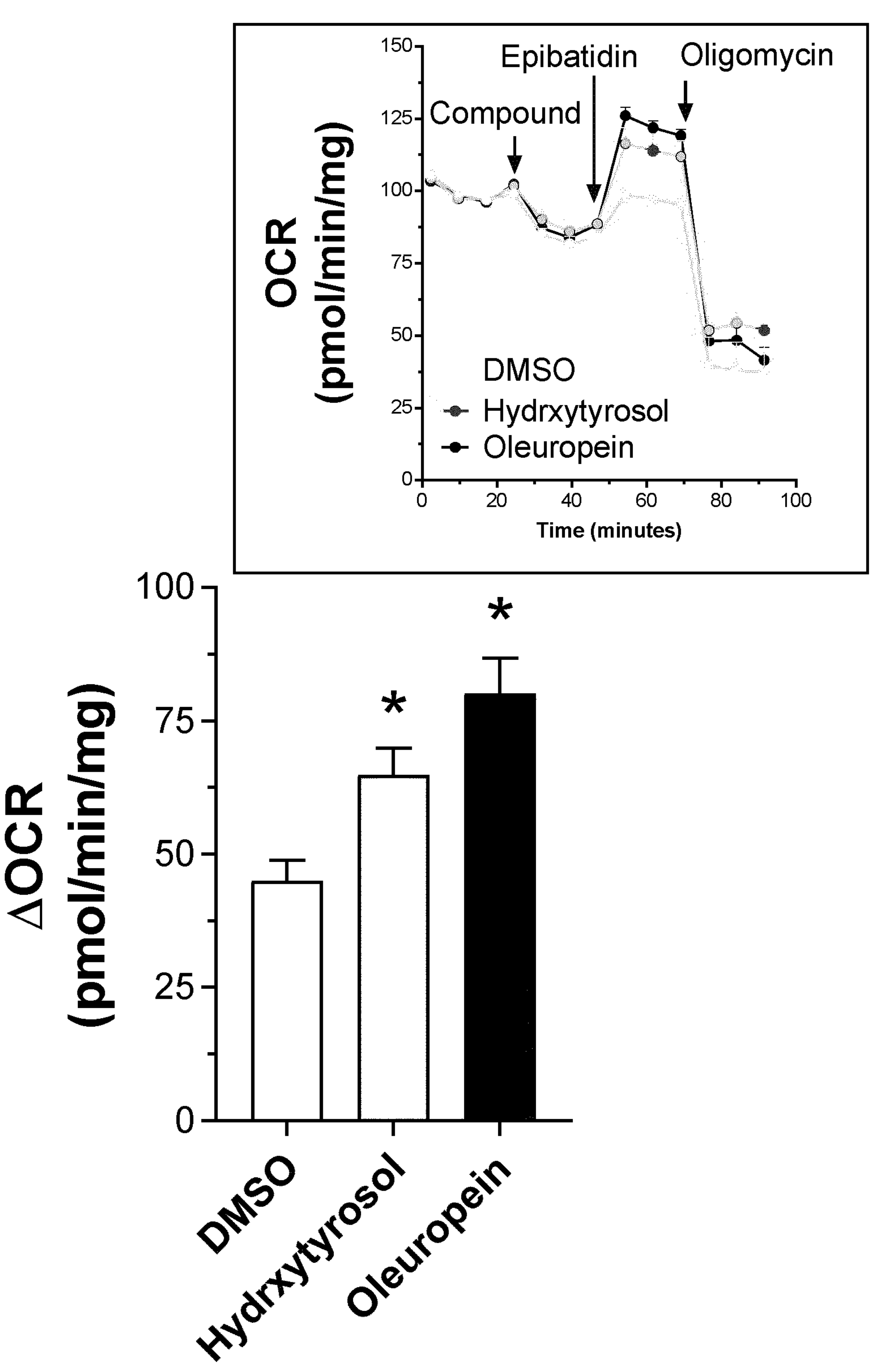
FIG. 9 is a graph showing that Oleuropein and hydroxytyrosol boost the ATP-synthase-dependent component of the respiration, during stimulation in myotubes, differentiated from human skeletal muscle (HSM) myoblasts. Statistical evaluation of the effect of 10 μM hydroxytyrosol (gray bar) or 10 μM oleuropein (black bar) on the ATP-synthase-dependent component of the respiration in HSM myotubes, stimulated with 10 μM epibatidine and calculated from the data in the inset. Inset, respiration profile of human skeletal muscle myotubes. The compounds are hydroxytyrosol or oleuropein. Oligomycin was used to determine the ATP-synthase dependent component of the respiration, in epipatidine-stimulated myotubes. Graph shows the average of 8 experiments. Results are expressed as mean+/−SEM. * indicates statistically significant difference vs. control (white bar) at $P<0.05$ (one-way ANOVA test).

As shown in FIG. 9, oleuropein and hydroxytyrosol boost the ATP-synthase-dependent component of the respiration, during stimulation in human skeletal muscle myotubes.

Example 3

Figure 10:
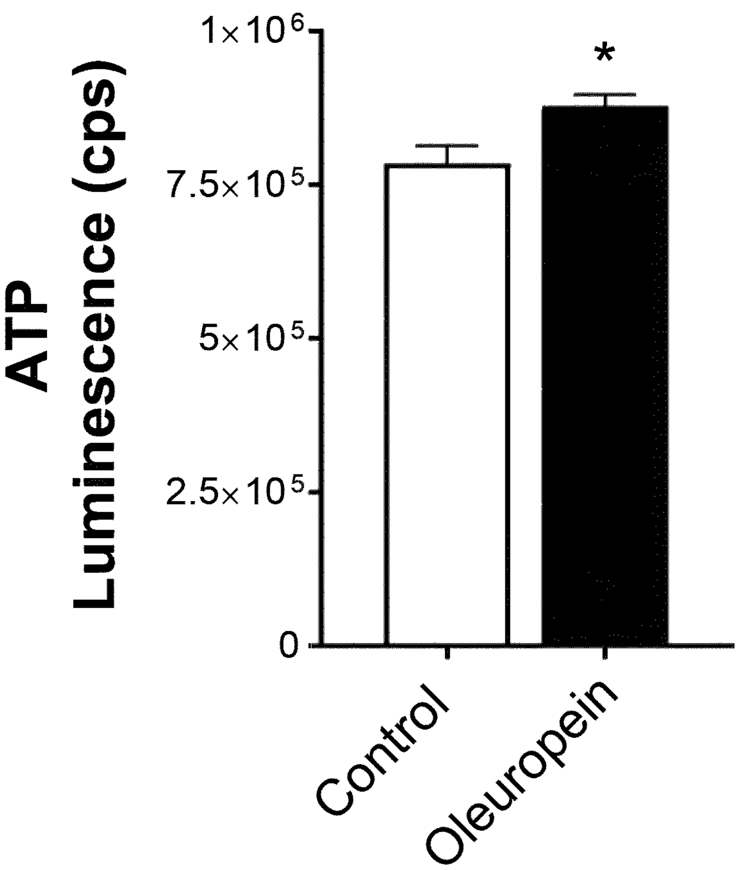
FIG. 10. is a graph showing that Oleuropein increases ATP production in C2C12-derived myotubes, stimulated with caffeine. Myotubes were incubated with oleuropein for 15 minutes, then they were stimulated with 5 mM caffeine for 10 minutes. Graph shows the average of 8 experiments. Results are expressed as mean+/−SEM. * indicates statistically significant difference vs. control cells (white) at $P<0.05$ (Student's t-test).

To test the effect of oleuropein on ATP production, the inventors measured ATP in myotubes differentiated from C2C12 cells. ATP was measured with conventional luminescence-based luciferin/luciferase method. Myotubes were incubated in KRBH medium and oleuropein was added for 15 minutes. Then myotubes were stimulated with 5 mM caffeine for additional 10 minutes. Finally, myotubes were incubated with luciferin/luciferase in lysis buffer and bioluminescence signal proportional to the amount of ATP present was measured at the Cytation 3 cell imaging reader (Biotek). As shown in FIG. 10 oleuropein increases ATP production in C2C12-derived myotubes, stimulated with caffeine.

Example 4

Figure 11:
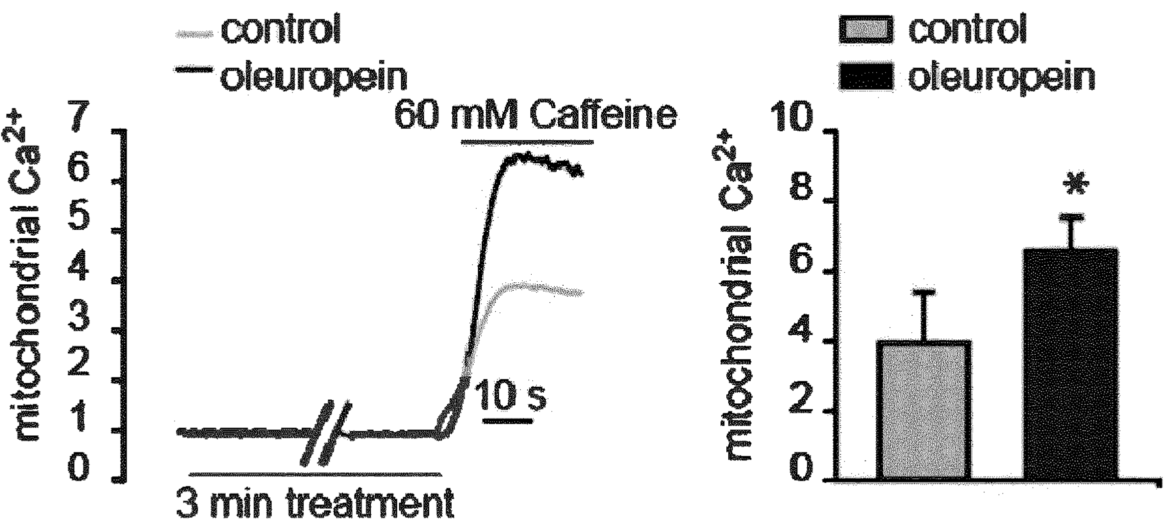
FIG. 11 is a graph showing that Oleuropein increases mitochondrial Calcium uptake in isolated adult mouse myofibers transfected with the mitochondrial calcium sensor 4mtGCaMP6f (ex vivo). Fibers were treated with oleuropein. Three minutes later, cells were stimulated with 60 mM caffeine. Left: representative traces of mitochondrial calcium uptake. Right: mean of mitochondrial calcium peak. Results are expressed as mean+/−SD. * indicates statistically significant difference vs. control myofibers at $P<0.05$ (Student's t-test), of >20 fibers per condition.
Figure 12:
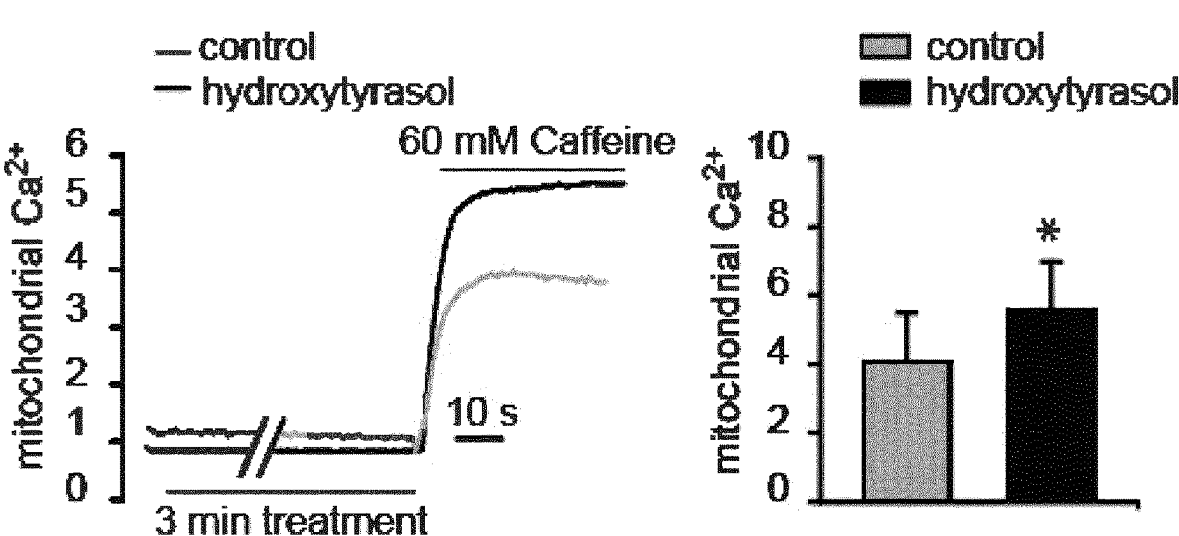
FIG. 12 is a graph showing that hydroxytyrosol increases mitochondrial Calcium uptake in isolated adult mouse myofibers transfected with the mitochondrial calcium sensor 4mtGCaMP6f (ex vivo). Fibers were treated with hydroxytyrosol. Three minutes later, cells were stimulated with 60 mM caffeine. Left: representative traces of mitochondrial calcium uptake. Right: mean of mitochondrial calcium peak. Results are expressed as mean+/−SD. * indicates statistically significant difference vs. control myofibers at $P<0.05$ (Student's t-test), of >20 fibers per condition.

To test the effect of oleuropein and hydroxytyrosol on mitochondrial calcium uptake in isolated adult mouse myofibers, flexor digitorum brevis (FDB) fibers were isolated 7-10 days after in vivo transfection. Muscles were digested in collagenase A (4 mg/ml) (Roche) dissolved in Tyrode's salt solution (pH 7.4) (Sigma-Aldrich) containing 10% fetal bovine serum (Thermo Fisher Scientific). Single fibers were isolated, plated on laminin-coated glass coverslips and cultured in DMEM with HEPES (42430 Thermo Fisher Scientific), supplemented with 10% fetal bovine serum, containing penicillin (100 U/ml), streptomycin (100 μg/ml). Fibers were maintained in culture at 37° C. with 5% $CO_2$. For mitochondrial $Ca^{2+}$ measurements, FDB muscles were electroporated with a plasmid encoding the mitochondrial calcium sensor 4mtGCaMP6f. After single fibers isolation, real time imaging was performed. During the experiments, myofibers were maintained in Krebs-Ringer modified buffer (135 mM NaCl, 5 mM KCl, 1 mM $MgCl_2$, 20 mM HEPES, 1 mM $MgSO_4$, 0.4 mM $KH_2PO_4$, 1 mM $CaCl_2$, 5.5 mM glucose, pH 7.4) at room temperature, in presence of 75 μM N-benzyl-P-toluenesulfonamide (BTS, Sigma-Aldrich) to avoid fiber contraction. 60 mM caffeine (Sigma-Aldrich) was added when indicated to elicit calcium release from intracellular stores. Experiments were performed on a Zeiss Axiovert 200 microscope equipped with a 40×/1.3 N.A. PlanFluor objective. Excitation was performed with a DeltaRAM V high-speed monochromator (Photon Technology International) equipped with a 75 W xenon arc lamp. Images were captured with a high-sensitivity Evolve 512 Delta EMCCD (Photometrics). The system is controlled by MetaMorph 7.5 (Molecular Devices) and was assembled by Crisel Instruments. 4mtGCaMP6f sensor was alternatively excited every second at 410 and 475 nm respectively and images were acquired through a dual band emission filter (520/40 and 630/60) (Chroma). Exposure time was set to 50 ms. Acquisition was performed at binning 1 with 200 of EM gain. Image analysis was performed with Fiji distribution of the ImageJ software. Images were background subtracted. As shown in FIG. 11 oleuropein increases mitochondrial calcium uptake in isolated adult mouse myofibers. As shown in FIG. 12 oleuropein increases mitochondrial calcium uptake in isolated adult mouse myofibers.

Example 5

Figure 13:
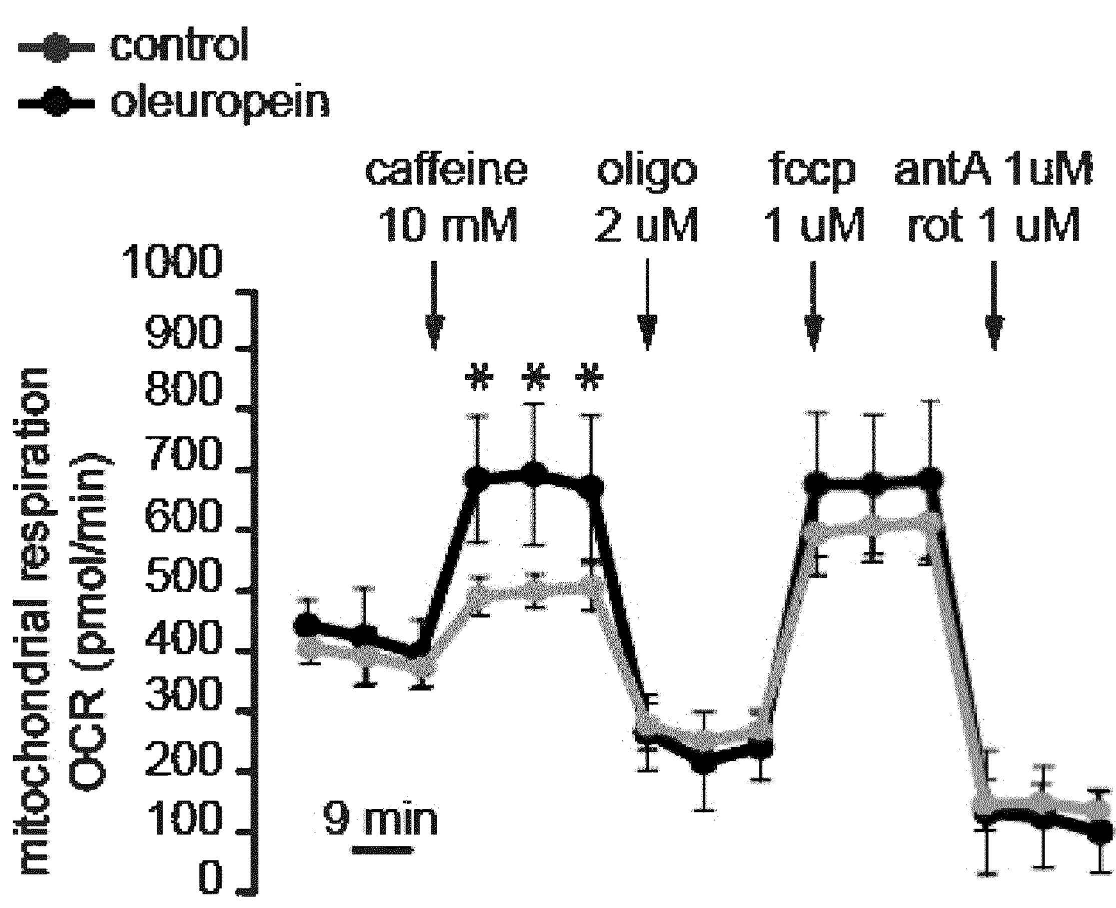
FIG. 13 is a graph showing that Oleuropein increases mitochondrial respiration in isolated adult mouse myofibers (ex vivo). Fibers treated with Oleuropein for 2 hours, were placed in a XF24 Extracellular Flux Analyzer (Agilent) to measure oxygen consumption rate upon caffeine stimulation. Oligomycin, FCCP and antimycin/rotenone were added consecutively to calculate basal, maximal, ATP-linked and non-mitochondrial respiration. Results are expressed as mean+/−SD. * indicates statistically significant difference vs. control myofibers at $P<0.05$ (Student's t-test) of 7 wells per condition.
Figure 14:
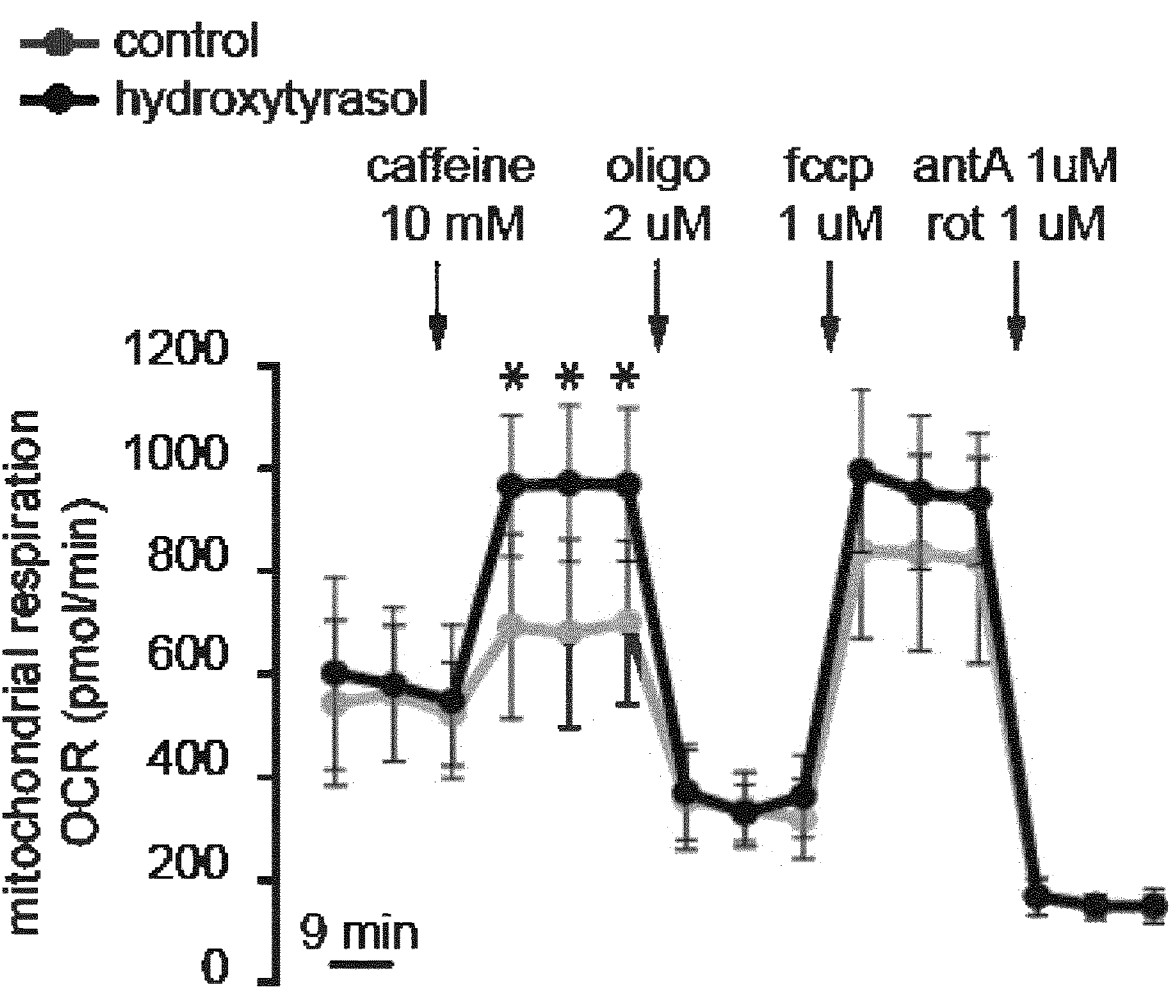
FIG. 14 is a graph showing that Hydroxytyrosol increases mitochondrial respiration in isolated adult mouse myofibers (ex vivo). Fibers treated with Hydroxytyrosol for 2 hours were placed in a XF24 Extracellular Flux Analyzer (Agilent) to measure oxygen consumption rate upon caffeine stimulation. Oligomycin, FCCP and antimycin/rotenone were added consecutively to calculate basal, maximal, ATP-linked and non-mitochondrial respiration. Results are expressed as mean+/−SD. * indicates statistically significant difference vs. control myofibers at $P<0.05$ (Student's t-test) of 7 wells per condition.

To test the effect of oleuropein and hydroxytyrosol on mitochondrial respiration in isolated adult mouse myofibers, flexor digitorum brevis (FDB) fibers were isolated as follows. Muscles were digested in collagenase A (4 mg/ml) (Roche) dissolved in Tyrode's salt solution (pH 7.4) (Sigma-Aldrich) containing 10% fetal bovine serum (Thermo Fisher Scientific). Single fibers were isolated, plated on laminin-coated XF24 microplate wells and cultured in DMEM (D5030 Sigma-Aldrich), supplemented with 1 mM Na Pyruvate, 5 mM glucose, 33 mM NaCl, 15 mg phenol red, 25 mM HEPES, 1 mM of L-Glu in presence of 75 μM N-benzyl-P-toluenesulfonamide (BTS, Sigma-Aldrich). Fibers were maintained for 2 hours in culture at 37° C. in 5% $CO_2$. The rate of oxygen consumption was assessed in real-time with the XF24 Extracellular Flux Analyzer (Agilent), which allows to measure oxygen consumption rate (OCR) changes after up to four sequential additions of compounds. A titration with the uncoupler FCCP was performed, in order to utilize the FCCP concentration (0.6 μM) that maximally increases OCR. To measure the effect of oleuropein or hydroxytyrosol on the stimulated respiration, fibers were stimulated with 10 mM caffeine. To evaluate the ATP-synthase-dependent component of the respiration, oligomycin (2 μM) was added. The results were normalized for the fluorescence of Calcein (Sigma-Aldrich). Fibers were loaded with 2 μM Calcein for 30 min. Fluorescence was measured using a Perkin Elmer EnVision plate reader in well scan mode using 480/20 nm filter for excitation and 535/20 nm filter for emission. As shown in FIG. 13, oleuropein increases the stimulated mitochondrial respiration and the ATP-synthase-dependent component of the respiration in isolated adult mouse myofibers. As shown in FIG. 14, hydroxytyrosol increases the stimulated mitochondrial respiration and the ATP-synthase-dependent respiration in isolated adult mouse myofibers.

Example 6

Figure 15:
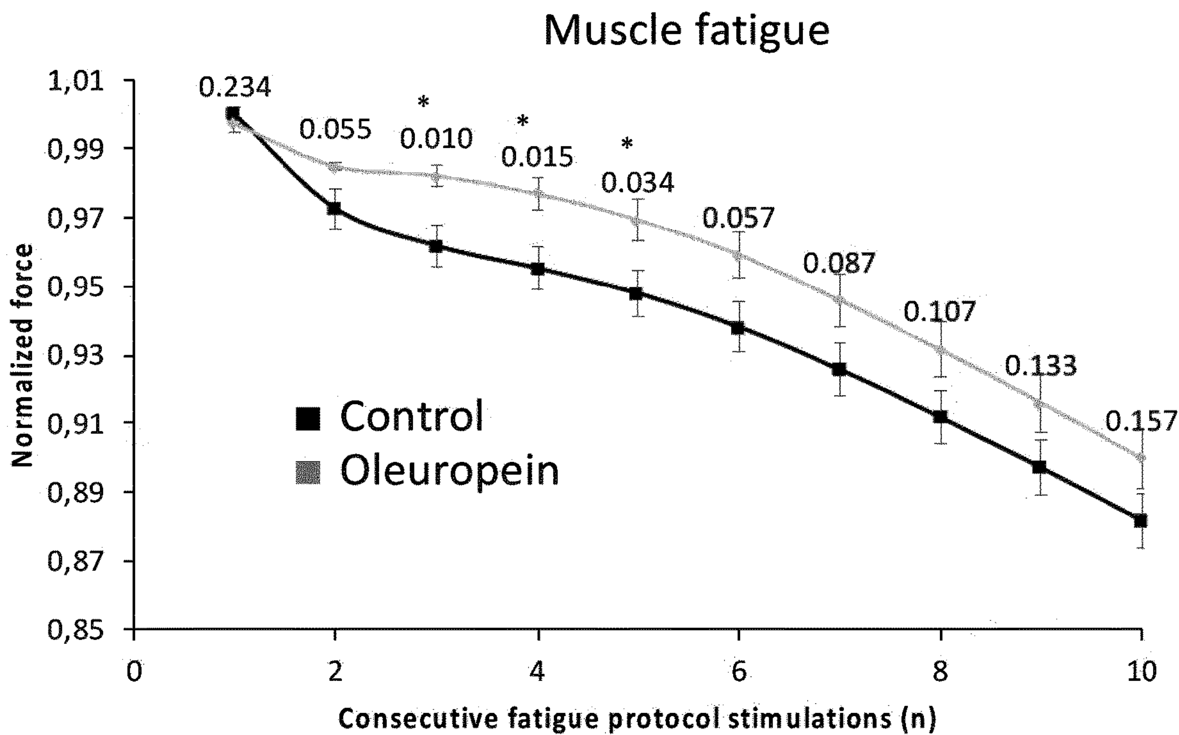
FIG. 15 is a graph showing that Oleuropein increases resistance to fatigue in mouse EDL (Extensor digitorum longus) muscle (ex vivo). Muscles incubated in Oleuropein show a significantly slower force reduction during fatigue than muscles in which DMSO was added. The third, fourth and fifth tetanic stimulation is significantly higher in Oleuropein compared to control, suggesting a higher resistance to fatigue. The P-value is shown at each tetanic contraction. Results are expressed as mean+/−SD. * indicates statistically significant difference vs. control muscles at $P<0.05$ (Student's t-test). Each experiment was repeated in 10 muscles for both experimental groups.

To test the effect of oleuropein on muscle fatigue in healthy adult mice, extensor digitorum longus (EDL) muscles were dissected from tendon to tendon under a stereomicroscope and mounted between a force transducer (KG Scientific Instruments, Heidelberg, Germany) in a small chamber in which oxygenated Krebs solution was continuously circulated and temperature maintained at 25° C. The stimulation conditions were optimized, and the length of the muscle was increased until force development during a 90 Hz stimulation was maximal. Oleuropein was added to the medium at a final concentration of 10 μM after the measurement of the first force-frequency relationship. Next, the force-frequency was determined every 10 minutes up to one hour after addition. After one hour, fatiguing protocol, which consisted of 120 tetanic contractions (100 Hz) with a duration of 300 ms repeated every second, was applied. Fatigue was determined as the force reduction relative to the initial force. Each experiment was repeated in 10 muscles for both experimental groups. As shown in FIG. 15, muscles incubated in oleuropein show a significantly slower force reduction during fatigue than in control muscles, indicating increased resistance to fatigue.

Example 7

Figure 16:
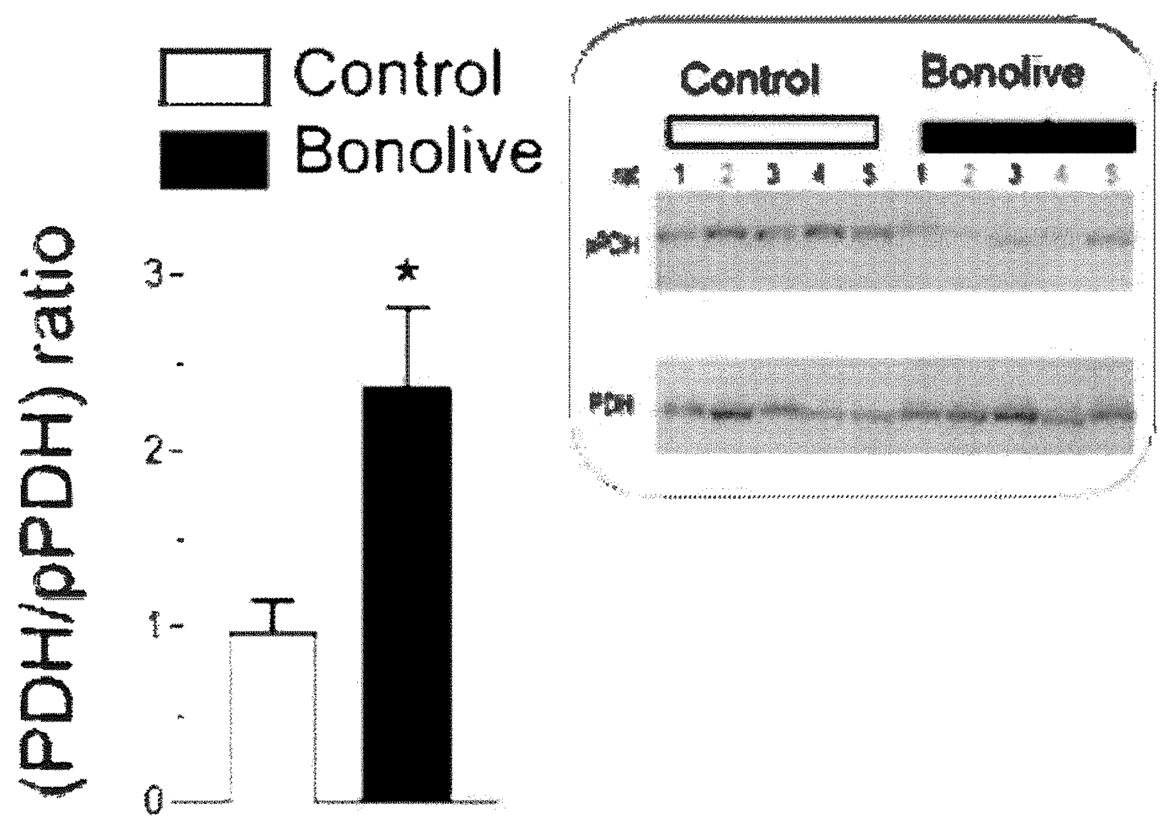
FIG. 16 is a graph showing that Bonolive® (BioActor BV, NL), an olive leaf extract standardised for its oleuropein content (≥40% oleuropeinand and <1% hydroxytyrosol (OHT)), promotes mitochondrial activation by dephosphorylation of Pyruvate dehydrogenase (PDH), in old rats treated for 3 months. The phospho-PDH and PDH levels were analyzed in gastrocnemius muscle in control and 3-months treated animals (inset). The activation of mitochondrial PDH was measured as the ratio between the total PDH and the phospho-PDH level. Graph shows the average of the muscle of 5 animals. Results are expressed as mean+/−SEM. * indicates statistically significant difference vs. control (white bar) at $P<0.05$ (Student's t-test).

To test the effect an olive leaf extract standardised for its oleuropein content (≥40% oleuropein), on mitochondrial activation by dephosphorylation of the pyruvate dehydrogenase (PDH), 20 months-old rats were supplemented for 3 months with Bonolive® (BioActor BV, NL), then the gastrocnemius muscles were analyzed by western. The content of PDH and phospho-PDH were quantified. To monitor protein levels, frozen muscles were pulverized by means of Qiagen Tissue Lyser and protein extracts were prepared in an appropriate buffer containing: muscle lysis buffer (50 mM Tris pH 7.5, 150 mM NaCl, 5 mM MgCl2, 1 mM DTT, 10% glycerol, 2% SDS, 1% Triton X-100, Complete EDTA-free protease inhibitor mixture (Roche), 1 mM PMSF, 1 mM NaVO3, 5 mM NaF and 3 mM β-glycerophosphate). 40 μg of total proteins were loaded, according to BCA quantification. Proteins were separated by SDS-PAGE electrophoresis, in commercial 4-12% acrylamide gels (Thermo Fisher Scientific) and transferred onto nitrocellulose membranes (Thermo Fisher Scientific) by wet electrophoretic transfer. Blots were blocked 1 hour at RT with 5% non-fat dry milk (Bio-Rad) in TBS-tween (0.5M Tris, 1.5M NaCl, 0.01% Tween) solution and incubated at 4° C. with primary antibodies. Secondary antibodies were incubated 1 hr at RT. The following antibodies were used: anti-phosphoPDH (1:5000, Abcam), anti-PDH (1:1000, Cell Signaling). Secondary HRP-conjugated antibodies were purchased from Bio-Rad and used at 1:5000 dilution. The activation of mitochondrial PDH was measured as the ratio between the total PDH and the phospho-PDH level. As shown in FIG. 16, Bonolive® (BioActor BV, NL), promotes mitochondrial activation by dephosphorylation of Pyruvate dehydrogenase, in old rats supplemented for 3 months with Bonolive® (BioActor BV, NL).

REFERENCES

Alvarez, J., & Montero, M. (2002). Measuring [Ca2+] in the endoplasmic reticulum with aequorin. Cell Calcium, 32(5-6), 251-260.

Montero, M., Lobaton, C. D., Hernandez-Sanmiguel, E., Santodomingo, J., Vay, L., Moreno, A., & Alvarez, J. (2004). Direct activation of the mitochondrial calcium uniporter by natural plant flavonoids. Biochem J, 384 (Pt 1), 19-24. doi:10.1042/BJ20040990.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treatment or prevention of a calcium deficiency/depletion disorder in an individual in need thereof, the method comprising orally administering to the individual a composition comprising an effective amount of a compound selected from the group consisting of oleuropein aglycone, homovanillyl alcohol, isohomovanillyl alcohol, and combinations thereof.

2. The method of claim 1, wherein the composition is orally administered daily for at least one week.

3. The method of claim 1, wherein the composition is selected from the group consisting of food compositions, dietary supplements, nutritional compositions, nutraceuticals, beverages, powdered nutritional products to be reconstituted in water or milk before consumption, food additives, medicaments, drinks, petfood, and combinations thereof.

4. The method of claim 1, wherein the composition further comprises calcium.

5. The method of claim 1, wherein the composition is a food product further comprising a component selected from the group consisting of protein, carbohydrate, fat, and combinations thereof.

6. The method of claim 4, wherein the composition comprises the calcium in an amount from about 200 mg to about 800 mg.

7. The method of claim 1, wherein the composition is administered for a time period of at least two days per week for at least two months.

8. The method of claim 1, wherein at least a portion of the effective amount of the compound is in the form of an extract.

9. The method of claim 8, wherein the extract is an Oleaceae plant extract.

10. The method of claim 5, wherein the protein comprises whey protein.

* * * * *